United States Patent [19]

Ahluwalia et al.

[11] Patent Number: 5,096,911

[45] Date of Patent: Mar. 17, 1992

[54] ALTERATION OF RATE AND CHARACTER OF HAIR GROWTH

[76] Inventors: Gurpreet S. Ahluwalia, 8632 Stable View Ct., Gaithersburg, Md. 20879; Douglas Shander, 16112 Howard Landing Dr., Gaithersburg, Md. 20878; F. Eugene Harrington, P.O. Box 200, 45 W. Main St., Newmarket, Md. 21774

[21] Appl. No.: 542,586

[22] Filed: Jun. 25, 1990

[51] Int. Cl.$^5$ .................. A61K 31/34; A61K 31/42; A61K 31/195
[52] U.S. Cl. .................. 514/380; 514/470; 514/563; 514/880
[58] Field of Search ............ 514/380, 470, 563, 880

[56] References Cited

U.S. PATENT DOCUMENTS 4,720,489  1/1988  Shander ........................ 514/171
4,885,289  12/1989  Breuer et al. .................. 514/170

FOREIGN PATENT DOCUMENTS 53-127432  2/1978  Japan .

OTHER PUBLICATIONS

Ebling, F. J., D. Sc., PhD., "Hair", Journal of Investigative Dermatology, 67:98-106, (1976).
Cardo, P. et al., "Cellular and Chemical Changes of Dermis Accompanying Physiologic and Pathologic Hair-Changes", Hair Research, 244-250 (1981).
Lucky, Anne W., M.D., "Topical Antiandrogens", Arch Dermatol, 121:55-56 (1985).
Goldbarg, Julius A., M.D. et al., "A Method for the Colorimetric Determination of Gamma-Glutamyl Transpeptidase in Human Serum; Enzymatic Activity in Health and Disease", 44:2:127-133, (1963).
Minato, Sadamasa, "Isolation of Anthglutin, an Inhibitor of Gamma-Glutamyl Transpeptidase from Penicillum Oxalicum", Archives of Biochemistry and Biophysics, 192:1:235-240 (1979).
Gardell, Stephen J. et al., "Affinity Labeling of Gamma-Glutamyl Tarnspeptidase by Glutamine Antagonists", Febs Letts, 122:2:171-174 (1980).
Reed, Donald J. et al., "The Inhibition of Gamma-Glutamyl Transpeptidase and Gluthathione Metabolism of Isolated Rat Kidney Cells by L-($\sigma$S,5-S)-$\sigma$-Amino-3-Chloro-4, 5-Dihydro-5-Isoxazoleacetic Acid (At-125; NSC-163501)", Biochemical and Biophysical Research Communications, 94:4:1273-1277, (1980).
Kim, Young Pio et al., "Gamma-Glutamyl Transpeptidase Activity in Human Skin", Journal of Dermatology, 6:39-45, (1979).
Lucky, Anne W. et al., "Hair Follicle Response of the Golden Syrian Hamster Flank Organ to Continuous Testosterone Stimulation Using Silastic Capsules", J. Investig. Dermatology, 86:83-86 (1986).
Kaszynski, Edwin, "Stimulation of Hair Growth in the Flank Organs of Female Hamsters by Subcutaneous Testosterone Propionate and Its Inhibition by Topical Cyproterone Acetate: Dose-Response Studies", Brit. J. Dermatology, 109:565-569 (1983).
Richards et al., "Expression of Gamma-Glutamyl Transpeptidase Activity in the Developing Mouse Tooth, Intervertebral Disc, and Hair Follicle", Cancer Research, 42:4143-4151 (1982).
Chase et al., "Critical Stages of Hair Development and Pigmentation in the Mouse", Physiological Zoology, 24:1-8 (1951).
De Young et al., "Localization and Significance of Gamma-Glutamyltranspeptidase in Normal and Neoplastic Mouse Skin", Cancer Research, 38:3697-3701 (1978).
Kinoshita et al., "The Synthesis of Antiglutin and Its Analogues", Bull. Chem. Soc. Jpn., 54:2219-2220 (1981).
Minato, "Isolation of Antiglutin, an Inhibitor of y--Glytamyl Transpeptidase from Penicillum Oxalicum", Archives of Biochemistry and Biophysics, 192:235-240 (1979).

Primary Examiner—Leonard Schenkman
Attorney, Agent, or Firm—Fish & Richardson

[57] ABSTRACT

The rate and character of mammalian hair growth is altered by the topical application to the skin of a composition containing an inhibitor of the enzyme gamma-glutamyl transpeptidase.

2 Claims, No Drawings

ALTERATION OF RATE AND CHARACTER OF HAIR GROWTH

This invention relates to a method and composition for altering the rate and character of mammalian hair growth, particularly androgen-stimulated hair growth, by topical application to the skin of a composition containing an inhibitor for gamma-glutamyl transpeptidase.

BACKGROUND OF THE INVENTION

It has previously been proposed to alter the rate and character of hair growth by applying to the skin inhibitors of certain enzymes such as inhibitors of 5-alpha-reductase or of ornithine decarboxylase, or such antiandrogen materials as cytoplasmic androgen receptor binding agents, as described in U.S. Pat. Nos. 4,720,489 and 4,885,289. Moreover, it has been theorized that other enzymes, including gamma-glutamyl transpeptidase, are involved in various stages of hair follicle formation or of hair growth, but the relation between the various enzymes and the reactions which they control, as well as their effect upon each other and upon hair growth, has not been fully understood, as appears from Richards et al, *Cancer Research*, Vol. 42, 4143–4152 (1982); DeYoung et al, *Cancer Research*, Vol. 38, 3697–3701 (1978); and Chase, *Physiolo. Zool.*, Vol. 24, 1–8 (1951).

It has now been found that the rate and character of mammalian (including human) hair growth, particularly androgen-stimulated hair growth, is altered by topical application to the skin of a composition containing an inhibitor of gamma-glutamyl transpeptidase.

Among the inhibitors of the enzyme gamma-glutamyl transpeptidase which can be used in the present invention are (alpha S,5S)-amino-3-chloro-4,5-dihydro-isoxazole acetic acid (acivicin); 1-gamma-L-glutamyl-2 (2-carboxyphenyl)-hydrazine (anthglutin); 5,5'-(4,5,6,7-tetrabromo-3-oxo-1(3H)- isobenzofuranylidene) bis[2-hydroxybenzenesulfonic acid](bromsulphalein); N-fumaroyl-L-2,3-diaminopropanoic acid (FDP); L-2-amino-4-oxo-5-chloropentanoic acid (chloroketone); and γ-glutamyl hydrazone of α-ketoglutarate. Of these, acivicin, anthglutin, and bromsulphalein are preferred. The composition contains, in addition to the inhibitor, a non-toxic dermatologically acceptable vehicle or carrier which is adapted to be spread upon the skin. The concentration of the inhibitor in the composition may be varied over a wide range up to a saturated solution, preferably from 0.1 to 20% by weight or even more; the reduction of hair growth increases as the amount of inhibitor applied increases per unit area of skin. The maximum amount effectively applied is limited only by the rate at which the inhibitor penetrates the skin. Generally, the effective amounts range from 10 to 2500 micrograms or more per square centimeter of skin.

The following specific examples are intended to illustrate more clearly the nature of the present invention without acting as a limitation upon its scope.

EXAMPLE 1

A vehicle or carrier was prepared having the following composition:

| Component | Wt. Percent Concentration |
|---|---|
| Water | 68% |
| Ethanol | 16% |
| Propylene Glycol | 5% |
| Dipropylene Glycol | 5% |
| Benzyl Alcohol | 4% |
| Propylene Carbonate | 2% |

Acivicin (Sigma Chemical Co., St. Louis) was mixed with separate portions of the foregoing vehicle to provide specimens containing 1,2, and 6% by weight respectively of the inhibitor and the pH was adjusted to pH 7.5 with sodium hydroxide.

Four groups (eight animals in each group) of male intact Golden Syrian hamsters were provided. These animals were considered acceptable models for human beard hair growth in that they display oval shaped flank organs, one on each side, each about 8 mm. in major diameter, which grow thick black and coarse hair similar to human beard hair. These organs produce hair in response to androgens in the hamster. The flank organs of each hamster were depilated by applying a thioglycolate- based chemical depilatory (Surgex), and to one organ of each animal was applied 10–25 mg. of vehicle alone once a day, while to the other organ of each animal was applied an equal amount of vehicle containing inhibitor. After three weeks of such applications (five days a week), the flank organs were shaved and the amount of recovered hair (hair mass) from each was weighed. The extent of reduction in hair growth by the inhibitor was expressed as the percent decrease in hair mass on the organ treated with inhibitor as compared to the organ treated with vehicle alone. As a control, one group of eight animals had both flank organs of each animal treated with vehicle alone. The results were as shown in Table 1 below.

TABLE 1

| | Inhibition of Hair Growth by Acivicin | | | |
|---|---|---|---|---|
| | | Hamster Flank Organ Hair Mass (mg) | | |
| Treatment Group | Concentration of the Active | Untreated (mean) | Treated (mean) | Percent Inhibition |
| Control | 0.00 | 0.58 | 0.61 | — |
| Acivicin | 1.0% | 1.04 | 0.85 | 18.2 |
| Acivicin | 2.0% | 1.33 | 0.56 | 57.9 |
| Acivicin | 6.0% | 0.79 | 0.15 | 81.0 |

The hair on the treated organ was also observed to be more vellus in nature than that on the untreated organ.

In addition, it was found that similar topical treatments with a 6% solution of acivicin over a three week period resulted in about 87% inhibition of follicle enzyme activity.

EXAMPLE 2

A composition was prepared containing 5% by weight of bromsulphalein disodium in the vehicle described in Example 1 above, and applied to hamster flank organs under the same conditions as described in Example 1. A 32% inhibition of hair mass was observed after three weeks.

EXAMPLE 3

Anthglutin, described as a specific inhibitor of gamma-glutamyl transpeptidase in Japanese Patent No. 53-127,432 and indicated to be an inhibitor of the enzyme gamma-glutamyl transpeptidase by Minato, *Archives Biochem. Biophy.*, Vol. 192, 235–240 (1979), was prepared by a procedure generally the same as that of Kinoshita et al, *Bull. Chem. Soc. Jpn.*, Vol. 54, 2219–2220 (1981). The synthesis was carried out in the following four steps:

1. 2-Hydrazinobenzoic acid

A solution of sodium acetate (21.7 g, 0.265 mol) in water (80 mL) is added to a solution of 2-hydrazinobenzoic acid hydrochloride (Aldrich, 50 g, 0.265 mol) in water (1500 mL), resulting in the formation of a thick precipitate. This mixture is refrigerated for three hours, filtered, washed with water (2×50 mL) and ethanol (1×100 mL) and dried under vacuum to give the free acid in 75% yield.

2. N-t-BOC-L-glutamic acid alpha-benzyl ester γ-2-hudrazinobenzoic acid amide The following reaction is run under a nitrogen atmosphere using pre-dried glassware. A solution of N,N'-dicyclohexylcarbodiimide (Aldrich, 16.9 g, 0.074 mol) in anhydrous methylene chloride (50 mL) is added to a solution of N-t-BOC-L-glutamic acid alpha-benzyl ester (Sigma, 25 g, 0.074 mol) and triethylamine (Aldrich, 10.4 g, 0.103 mo)) in anhydrous methylene chloride (!50 mL). To this solution is added a slurry of 2-hydrazinobenzoic acid (23 g, 0.151 mol) in anhydrous methylene chloride (500 mL). The reaction mixture is stirred at room temperature overnight and filtered through a pad of Celite 545. The filtrate is evaporated under vacuum, redissolved in methylene chloride (250 mL), and washed with water (3×100 mL). The organic layer is evaporated under vacuum and the resulting residue is purified by recrystallization in ethanol/water to give the desired compound in 30% yield.

3. N-t-BOC-L-glutamic acid γ-2-hvdrazinobenzoic acid amide

The following reaction is run under a nitrogen atmosphere using pre-dried glassware. Palladium on carbon catalyst (Aldrich, 5% C, 4.5 g) is added to a solution of the product in step 2 (10 g, 0.02 mol) and cyclohexene (Aldrich, 12 mL) in absolute ethanol (225 mL). The mixture is refluxed for three hours, cooled, and filtered through a pad of Celite 545. The filtrate is evaporated under vacuum to give the desired compound in greater than 90% yield.

4. Preparation of 1-γ-L-glutamvl-2-(2-carboxyphenvl) hydrazine-Anthglutin

The following reaction is run under a nitrogen atmosphere using pre-dried glassware. The product from step 3 (7.1 g, 0.02 mol), anisole (Aldrich, 29.6 g, 0.26 mole), and trifluoroacetic acid (Aldrich, 5 g, 0.046 mol) are stirred at 0° C. for three hours. Ethyl ether (300 mL) is added to the reaction solution and the resulting gummy precipitate is triturated with additional ethyl ether to produce crude anthglutin as a white powder in 40% yield. The crude product is further purified via ion-exchange chromatography on a Dowex 2×8 anion exchange column, yielding 240 mg of slightly yellow crystalline product which exhibited UV absorption maxima ($\lambda$ max) at pH2 and pHλ of 320 and 306 nm, in close agreement with the values reported in the literature.

The anthglutin prepared as described above was dissolved in specimens of the vehicle described in Example 1 and applied to the flank organs of groups of hamsters in the same manner as described in Example 1, a group of eight animals being used for each different composition. The results were as follows:

TABLE 2

| Treatment Group | Concentration of the Active | Hamster Flank Organ Hair Mass (mg) | | Percent Inhibition |
|---|---|---|---|---|
| | | Untreated (mean) | Treated (mean) | |
| Control | 0.00 | 2.66 | 2.33 | — |
| Anthglutin | 0.5% | 2.03 | 1.81 | 10.7 |
| Anthglutin | 1.0% | 1.92 | 1.60 | 16.7 |
| Anthglutin | 2.0% | 2.57 | 1.58 | 38.6 |
| Anthglutin | 6.0% | 2.26 | 0.74 | 67.2 |

Anthglutin was also found to inhibit the activity of hair follicle gamma-glutamyl transpeptidase, for which the anthglutin had a strong inhibitory affinity.

Similar results can be expected for other inhibitors of gamma-glutamyl transpeptidase.

What is claimed is:

1. The process of reducing the rate and altering the character of mammalian hair growth which comprises the step of applying to the skin a composition containing an inhibitor of gamma-glutamyl transpeptidase, at a rate of 10 to 2500 micrograms of said inhibitor per square centimeter of skin.

2. The process as claimed in claim 1 in which said inhibitor is selected from the group consisting of acivicin, bromsulphalein, and anthglutin.

* * * * *